United States Patent [19]

Axen

[11] 4,251,466

[45] Feb. 17, 1981

[54] 2-DECARBOXY-2-HYDROXYMETHYL-6-KETO-PGE$_1$ COMPOUNDS

[75] Inventor: Udo F. Axen, Plainwell, Mich.

[73] Assignee: The Upjohn Company, Kalamazoo, Mich.

[21] Appl. No.: 70,233

[22] Filed: Aug. 27, 1979

Related U.S. Application Data

[60] Division of Ser. No. 829,679, Sep. 2, 1977, which is a continuation-in-part of Ser. No. 755,675, Dec. 30, 1976, abandoned.

[51] Int. Cl.$^3$ .................. C07C 49/743; C07C 49/753; C07C 49/747
[52] U.S. Cl. .................................... 568/330; 568/379; 568/380
[58] Field of Search ..................... 260/586 R; 568/330

[56] References Cited

U.S. PATENT DOCUMENTS 4,131,738  12/1978  Smith .................................. 560/121

OTHER PUBLICATIONS

Tanaka et al., "Tett. Letters", p. 1535, (1975).

*Primary Examiner*—Joseph E. Evans
*Attorney, Agent, or Firm*—Robert A. Armitage

[57] ABSTRACT

Prostaglandin E (PGE)-type derivatives and analogs having a 6-keto feature are disclosed, including processes for preparing them and the appropriate intermediates, said derivatives having pharmacological activity.

37 Claims, No Drawings

2-DECARBOXY-2-HYDROXYMETHYL-6-KETO-PGE₁ COMPOUNDS

CROSS REFERENCE TO RELATED APPLICATIONS

This application is a divisional application of co-pending application Ser. No. 829,679, filed Sept. 2, 1977, now pending issuance; which is a continuation-in-part of Ser. No. 755,675, filed Dec. 30, 1976, now abandoned.

DESCRIPTION

BACKGROUND OF THE INVENTION

The present invention relates to novel 2-decarboxy-2-hydroxymethyl-6-keto-PGE₁ compounds which are useful agents for the induction of prostacyclin-like pharmacological effects. Accordingly, these compounds are useful for pharmacological purposes for which prostacyclin and related substances are employed. The essential material constituting disclosure of the preparation and use of these novel compounds is incorporated here by reference from Ser. No. 829,679, filed Sept. 2, 1977.

SUMMARY OF THE INVENTION

The present invention particularly provides a compound of the formula

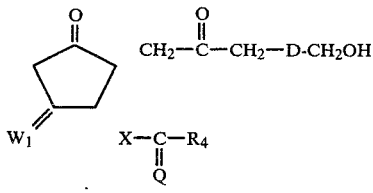

wherein $W_1$ is $\alpha$-OH:$\beta$-H, $\beta$-H:$\beta$-OH, $\alpha$-H:$\beta$-H, methylene, or $\alpha$-CH₂OH:$\beta$-H;
wherein Q is oxo, $\alpha$-H:$\beta$-H, $\alpha$-R₈:$\beta$-OH, or $\alpha$-OH:$\beta$-R₈, wherein R₈ is hydrogen or alkyl of one to 4 carbon atoms, inclusive;
wherein R₄ is
(1) —C(R₅)(R₆)—C$_g$H$_{2g}$—CH₃
(2) —C(R₅)(R₆)—Z—(Ph) or
(3) cis-CH₂-CH=CH-CH₂CH₃,
wherein C$_g$H$_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or C$_j$H$_{2j}$ is a valence bond or alkylene of one to 9 carbon atoms, inclusive, with one to 6 carbon atoms, inclusive between CR₅R₆— and the (Ph); wherein (Ph) is phenyl or phenyl substituted by (T)s,
wherein T is alkyl of one to 4 carbon atoms, inclusive, fluoro, chloro, trifluoromethyl, or —OR₇, wherein R₇ is alkyl of one to 4 carbon atoms, inclusive,
wherein s is zero, one, 2 or 3, with the proviso that not more than two T's are other than alkyl and when s is 2 or 3 the T's are either the same or different;
wherein D is (1) —(CH₂)$_d$—C(R₂)₂—
(2) —CH₂—O—CH₂—Y— or
(3) —CH₂—CH=CH—
wherein d is zero to 5, R₂ is hydrogen, methyl, or fluoro, being the same or different with the proviso that one R₂ is not methyl when the other is fluoro, and Y is a valence bond, —CH₂— or —(CH₂)₂—, and
wherein X is
(1) trans—CH=CH—
(2) cis—CH=CH—
(3) —C≡C—
(4) —CH₂CH₂—.

With regard to the divalent substituents described above, e.g., Q and W₁, these divalent radicals are defined as $\alpha$-R$_i$:$\beta$-R$_j$, where Ri represents a substituent of the divalent moiety of the alpha configuration with respect to the cyclopentane ring and R$_j$ represents a substituent to the divalent moiety of the beta configuration with respect to the cyclopentane ring. Accordingly, when Q is defined as $\alpha$-OH:$\beta$-R₈, the hydroxy of the Q moiety is in the alpha configuration, i.e. as in prostacyclin, and the R₈ substituent is in the beta configuration. Not all carbon atoms to which such divalent moieties are attached represent asymmetric centers. For example, when both valence bonds are to hydrogen (e.g., W₁ or Q is $\alpha$-H:$\beta$-H), then no asymmetric center is present.

DESCRIPTION OF THE PREFERRED EMBODIMENTS

The present invention particularly relates to the following chemical compounds:
2-decarboxy-2-hydroxymethyl-6,15-diketo-PGE₁;
2-decarboxy-2-hydroxymethyl-6-keto-PGE₁;
2-decarboxy-2-hydroxymethyl-16,16-dimethyl-6-keto-PGE₁;
2-decarboxy-2-hydroxymethyl-16-phenoxy-17,18,19,20-tetranor-6-keto-PGE₁;
2-decarboxy-2-hydroxymethyl-16-phenyl-17,18,19,20-tetranor-6-keto-PGE₁;
2-decarboxy-2-hydroxymethyl-17-phenyl-18,19,20-trinor-6-keto-PGE₁;
2-decarboxy-2-hydroxymethyl-15(S)-15-methyl-6-keto-PGE₁;
2-decarboxy-2-hydroxymethyl-(15R)-15-methyl-6-keto-PGE₁;
2-decarboxy-2-hydroxymethyl-6-keto-13,14-didehydro-PGE₁;
2-decarboxy-2-hydroxymethyl-6-keto-13,14-didehydro-(15R)-PGE₁;
2-decarboxy-2-hydroxymethyl-6-keto-13,14-dihydro-PGE₁;
2-decarboxy-2-hydroxymethyl-2,2-difluoro-6-keto-PGE₁;
2-decarboxy-2-hydroxymethyl-2,2-difluoro-16,16-dimethyl-6-keto-PGE₁;
2-decarboxy-2-hydroxymethyl-2,2-difluoro-16-phenoxy-17,18,19,20-tetranor-6-keto-PGE₁;
2-decarboxy-2-hydroxymethyl-2,2-difluoro-(15S)-15-methyl-6-keto-PGE₁;
2-decarboxy-2-hydroxymethyl-2,2-difluoro-13,14-didehydro-6-keto-PGE₁; and
2-decarboxy-2-hydroxymethyl-2,2-difluor-13,14-dihydro-6-keto-PGE₁.

I claim:
1. A compound of the formula

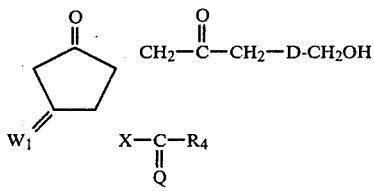

wherein $W_1$ is α-OH:β-H, α-Hβ-OH, α-H:β-H, methylene, or α-CH$_2$OH:β-H;

wherein Q is oxo, α-H:β-H, α-R$_8$:βα-OH, or α-OH:β-R$_8$, wherein R$_8$ is hydrogen or alkyl of one to 4 carbon atoms, inclusive;

wherein R$_4$ is
(1) —C(R$_5$)(R$_6$)—C$_g$H$_{2g}$—CH$_3$
(2) —C(R$_5$)(R$_6$)—Z—(Ph) or
(3) cis—CH$_2$—CH=CH—CH$_2$CH$_3$, wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by (T)s, wherein T is alkyl of one to 4 carbon atoms, inclusive, fluoro, chloro, trifluoromethyl, or —OR$_7$— wherein R$_7$ is alkyl of one to 4 carbon atoms, inclusive, and wherein s is zero, one, 2 or 3, with the proviso that not more than two T's are other than alkyl and when s is 2 or 3 the T's are either the same or different;

wherein D is
(1) —(CH$_2$)$_d$—C(R$_2$)$_2$—
(2) —CH$_2$—O—CH$_2$—Y— or
(3) —CH$_2$CH=CH— wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—, and wherein X is
(1) trans—CH=CH—
(2) cis—CH=CH—
(3) —C≡C—
(4) —CH$_2$CH$_2$—.

2. A compound according to claim 1 wherein $W_1$ is α-OH:β-H.

3. A compound according to claim 2 wherein D is —(CH$_2$)$_d$—C(R$_2$)$_2$— wherein d and R$_2$ are as defined in claim 1.

4. A compound according to claim 3 wherein D is —(CH$_2$)$_3$—.

5. A compound according to claim 4 wherein X is trans-CH=CH—.

6. A compound according to claim 5 wherein Q is oxo.

7. 2-Decarboxy-2-hydroxymethyl-15-deoxy-6,15-diketo-PGE$_1$, a compound according to claim 6.

8. A compound according to claim 5 wherein Q is α-OH:β-R$_8$, wherein R$_8$ is hydrogen, methyl or ethyl.

9. A compound according to claim 8 wherein R$_8$ is hydrogen.

10. 2-Decarboxy-2-hydroxymethyl-6-Keto-PGE$_1$, a compound according to claim 9.

11. 2-Decarboxy-2-hydroxymethyl-16,16-dimethyl-6-keto-PGE$_1$, a compound according to claim 9.

12. 2-Decarboxy-2-hydroxymethyl-16-phenoxy-17,18,19,20-tetranor-6-keto-PGE$_1$, a compound according to claim 9.

13. 2-Decarboxy-2-hydroxymethyl-16-phenyl-17,18,19,20-tetranor-6-keto-PGE$_1$, a compound according to claim 9.

14. 2-Decarboxy-2-hydroxymethyl-17-phenyl-18,19,20-trinor-6-keto-PGE$_1$, a compound according to claim 9.

15. A compound according to claim 8 wherein R$_8$ is methyl.

16. 2-Decarboxy-2-hydroxymethyl-15(S)-15-methyl-6-keto-PGE$_1$, a compound according to claim 15.

17. A compound according to claim 5 wherein Q is α-R$_8$:β-OH, wherein R$_8$ is hydrogen, methyl or ethyl.

18. 2-Decarboxy-2-hydroxymethyl-(15R)-15-methyl-6-keto-PGE$_1$, a compound according to claim 17.

19. A compound according to claim 4 wherein X is —C≡C—.

20. A compound according to claim 19 wherein Q is α-OH:β-R$_8$, wherein R$_8$ is hydrogen, methyl or ethyl.

21. 2-Decarboxy-2-hydroxymethyl-6-keto-13,14-didehydro-PGE$_1$, a compound according to claim 20.

22. A compound according to claim 19 wherein Q is α-R$_8$:β-OH wherein R$_8$ is hydrogen, methyl or ethyl.

23. 2-Decarboxy-2-hydroxymethyl-6-keto-13,14-didehydro-(15R)-PGE$_1$, a compound according to claim 22.

24. A compound according to claim 4 wherein X is —CH$_2$CH$_2$—.

25. 2-Decarboxy-2-hydroxymethyl-6-keto-13,14-dihydro-PGE$_1$, a compound according to claim 24.

26. A compound according to claim 3 wherein D is —(CH$_2$)$_2$—CF$_2$—.

27. A compound according to claim 26 wherein X is trans—CH=CH—.

28. A compound according to claim 27 wherein Q is α-OH:β-H.

29. 2-Decarboxy-2-hydroxymethyl-2,2-difluoro-6-keto-PGE$_1$, a compound according to claim 28.

30. 2-Decarboxy-2-hydroxymethyl-2,2-difluoro-16,16-dimethyl 6-keto-PGE$_1$, a compound according to claim 28.

31. 2-Dicarboxy-2-hydroxymethyl-2,2-difluoro-16-phenoxy-17,18,19,20-tetranor-6-keto-PGE$_1$, a compound according to claim 28.

32. A compound according to claim 27 wherein Q is α-OH:β-CH$_3$.

33. 2-Decarboxy-2-hydroxymethyl-2,2-difluoro-(15S)-15-methyl-6-keto-PGE$_1$, a compound according to claim 32.

34. A compound according to claim 26 wherein X is —C≡C—.

35. 2-Decarboxy-2-hydroxymethyl-2,2-difluoro-13,14-didehydro-6-keto-PGE$_1$, a compound according to claim 34.

36. A compound according to claim 26 wherein X is —CH$_2$CH$_2$—.

37. 2-Decarboxy2-hydroxymethyl-2,2-difluoro-13,14-dihydro-6-keto-PGE$_1$, a compound according to claim 36.

* * * * *

UNITED STATES PATENT OFFICE
CERTIFICATE OF CORRECTION

Patent No. 4,251,466              Dated 17 February 1981

Inventor(s) Udo F. Axen

It is certified that error appears in the above-identified patent and that said Letters Patent are hereby corrected as shown below:

In Related U.S. Application Data: "Ser. No. 829,679, Sep. 2, 1977" should read -- Ser. No. 829,679, Sep. 2, 1977, U.S. Patent 4,205,178 --;

Column 1, line 9, "now pending issuance;" should read -- now U.S. Patent 4,205,178; --;

Column 1, lines 30-35, and Column 3, lines 1-9, the formula should read as follows instead of as appears in the patent:

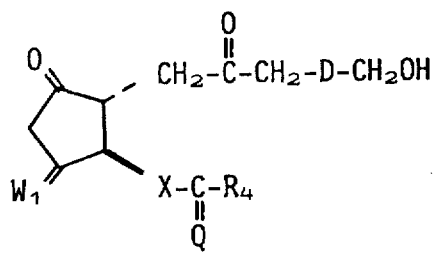

Column 1, line 39, "β-H:β-OH," should read -- α-H:β-OH, --;
Column 2, line 35, "-6,15-diketo-PGE$_1$;" should read -- -15-deoxy-6,15-diketo-PGE$_1$; --;
Column 3, line 10, "α-Hβ-OH" should read -- α-H:β-OH --; line 12, "α-R$_8$:βα-OH," should read -- α-R$_8$:β-OH, --.

Signed and Sealed this

Ninth Day of June 1981

[SEAL]

Attest:

RENE D. TEGTMEYER

Attesting Officer    Acting Commissioner of Patents and Trademarks